United States Patent [19]

Pena et al.

[11] Patent Number: 4,938,953
[45] Date of Patent: Jul. 3, 1990

[54] SELF-PRESERVING CONDITIONING SHAMPOO FORMULATION

[75] Inventors: Lorraine E. Pena, Kalamazoo; Jenny L. Peters, Mattawan, both of Mich.

[73] Assignee: The Upjohn Company, Kalamazoo, Mich.

[21] Appl. No.: 230,176

[22] Filed: Aug. 9, 1988

[51] Int. Cl.$^5$ .............................................. A61K 7/075
[52] U.S. Cl. ................................ 424/70; 252/DIG. 13
[58] Field of Search .................. 424/70; 252/550, 544, 252/546, 547, DIG. 13

[56] References Cited

U.S. PATENT DOCUMENTS

| | | | |
|---|---|---|---|
| 4,075,131 | 2/1978 | Sterling | 424/70 X |
| 4,497,825 | 2/1985 | Bade | 252/544 X |
| 4,595,526 | 6/1986 | Lai | 252/550 X |
| 4,772,424 | 9/1988 | Greeb | 252/550 X |

OTHER PUBLICATIONS

"Shampoo Formulary" Cosmetics & Toiletries, vol. 103, Mar. 1988.
Garrand, V. A., "Antimicrobial Properties of a Cocoamidopropyl Betaine", Cosmetics & Toiletries, vol. 100, pp. 77–80 (Feb. 1985).

Primary Examiner—Thurman K. Page
Assistant Examiner—Susan S. Rucker
Attorney, Agent, or Firm—Donald L. Corneglio

[57] ABSTRACT

A conditioning shampoo formulation comprising a base surfactant level of at least 16%, which includes cocamidopropyl betaine and cocamide diethanolamine. The formulation is essentially free of additional preservatives and is suitable for use as a conditioner for hair prior to treatment with a hair restoring medication or agent.

8 Claims, No Drawings

SELF-PRESERVING CONDITIONING SHAMPOO FORMULATION

BACKGROUND OF THE INVENTION

The present invention is directed to a conditioning shampoo formulation having a high surfactant level suitable for preconditioning thinning hair prior to treatment with a hair restorer. The formulation is further characterized by comprising three main ingredients: (1) a fatty alcohol sulfate such as triethanolamine lauryl sulfate or sodium lauryl sulfate and/or a fatty alcohol ether sulfate such as sodium laureth sulfate; (2) cocamidopropyl betaine and (3) cocamide diethanolamine, which are formulated in the absence of addtional preservative compounds.

Shampoos are a mixture of various types of surfactants which impart different characteristics to the final product. In general, a shampoo contains a base surfactant(s) for cleansing at 10–15% (w/w), a foam booster at 3–5% (w/w), a conditioning agent at 3–5% (w/w), small amounts of chelating agents, viscosity and pH adjusters, preservatives, fragrance, miscellaneous "nutritive" ingredients, and water.

The base surfactant is usually a salt of a $C_{12}$–$C_{14}$ alkyl sulfate, alkyl ether sulfate, or alkyl olefin sulfonate, depending on the mildness and foaming characteristics desired. "Baby" shampoos and "extra gentle" shampoos will usually use an emphoteric, nonionic, or sulfosuccinate as a base surfactant. The foam boosters are primarily $C_{12}$–$C_{14}$ fatty alkanolamide surfactants derived from coconut oils. The conditioning agents generally are substantive to the hair and frequently serve a dual role as a foam booster. Cocamidopropyl betaine and coconut oil derived amine oxides are typical examples of surfactant based conditioning agents. Hydrolyzed animal protein, keratin, and collagens have been popular conditioning agents for many years. The base surfactants and conditioning agents are usually sold as solutions in the range of 20–40% (w/w). The percentages specified above are on the "as is" basis as purchased from the supplier rather than on the "active" basis. Thus, the percentages specified above may contain a substantial amount of water.

Due to the nature of the composition, a shampoo is usually a good medium to support microbial growth. Since most surfactants used in the manufacture of shampoos are sold as aqueous solutions or pastes, which are rarely more than 40% (w/w) on the active basis, they will support microbial growth and are frequently preserved with trace levels of formaldehyde by the supplier. The foam boosters and conditioning agents provide a good nitrogen source to the microbes in the aqueous enviroment of the shampoo which is typically greater than 80% water. Proteins and "nutrient" ingredients are particularly good microbial growth promoters and a present a challenge to selection of an effective preservative system. Surprisingly, the subject formulation is high in surfactant but does not support microbial growth and, therefore is self-preserving without the addition of traditional preservatives.

INFORMATION DISCLOSURE STATEMENT

The present invention has devised a high surfactant shampoo which is free of additional preservative compounds. The formulation does employ cocamidopropyl betaine which has been reported to have antimicrobial properties but has been more traditionally used as a conditioning or foam boosting agent, Garrand, V.A., *Antimicrobial Properties of a Cocamidopropyl Betaine*, Cos. & Toiletries, 100, 77 (Feb. 1985).

SUMMARY OF THE INVENTION

The present invention is directed toward a conditioning shampoo formulation comprising (a) a fatty alcohol sulfate and/or fatty alcohol-ether sulfate in an amount of at least 10% w/w, (b) cocamidopropyl betaine, and (c) cocamide diethanolamine; wherein the total amount of said (a), (b) and (c) is at least 16% (w/w) and wherein said formulation is essentially free of additional preservatives. Component (a) can be selected from the group consisting of triethanolamine lauryl sulfate, sodium lauryl sulfate or sodium laureth sulfate, preferably triethanolamine lauryl sulfate and sodium laureth sulfate.

In one preferred embodiment the components (a), (b) and (c) are present in a total amount of about 30% w/w. Component (b) can be present in an amount of from about 0.5 to about 3% w/w. Component (c) can be is present in an amount from about 2 to about 7% w/w.

In one preferred formulation, the shampoo can comprise about 14% triethanolamine lauryl sulfate, about 6% sodium laureth sulfate, about 1.5% cocamidopropyl betaine, and about 5% cocamide diethanolamine. In another preferred formulation, the shampoo can comprise about 3% triethanolamine lauryl sulfate, about 7% sodium laureth sulfate, about 2% cocamidopropyl betaine and about 4% cocamide diethanolamine. In yet another preferred formulation, the shampoo can comprise about 16% triethanolamine lauryl sulfate, about 7% sodium laureth sulfate, about 1.5% cocamidopropyl betaine, and about 5% cocamide diethanolamine.

The conditioning shampoo formulation is especially suitable for use by individuals who are applying a medication or treatment to their hair. The high surfactant level deep cleans the hair to provide an excellent environment for a medication or treatment to be absorbed by the hair and scalp.

DETAILED DESCRIPTION OF THE INVENTION

The present invention is a high surfactant conditioning shampoo. Typical shampoos contain from about 10 to 15% surfactant on the active basis whereas the subject formulation contains at least 16% surfactant. All percentages are on a weight per weight (w/w) active basis. This conditioning shampoo is especially adapted for use on a regular basis for individuals with thinning hair prior to the application of a hair restorer such as minoxidil.

The surfactant content of the shampoo formulation is at least 16%, preferably from 16 to about 30%. The base surfactants used are fatty alcohol sulfates such as triethanolamine lauryl sulfate or sodium lauryl sulfate and fatty alcohol ether sulfates such as sodium laureth sulfate. These surfactants are commonly available and are formulated in amounts such that the total base surfactant level in the shampoo is at least 10%.

The shampoo formulation also contains cocamidopropyl betamine which is a common shampoo ingredient used as a conditioning agent or foam booster to enhance the richness of the lather. Typically, the cocamidopropyl betaine is added in an amount of from about 0.5 to about 3%, more preferably from about 1.5 to about 2%.

The third essential ingredient is cocamide diethanolamine which is a common shampoo ingredient frequently used as a foam booster. This ingredient is present in an amount of from about 2 to about 7%, more preferably 3 to about 5%.

In addition to the above three ingredients, the shampoo can contain other components normally associated with shampoo formulation with the proviso that no additional preservatives are included. Thus, with the exception of those compounds present in trace amounts in the surfactants such as formaldehyde and the known propensity for cocamidopropyl betaine to have antimicrobial activity, the subject formulation is essentially free of traditionally used preservatives. Typical additional ingredients can include viscosity controlling agents such as sodium chloride and propylene glycol, opacifying agents, clarifying agents, acidifying agents such as citric acid and fragrance.

An important characteristic of the subject formulation is the inherent preservative quality which is demonstrated below in the following examples.

EXAMPLE 1

The following formalation is an apporoximately 29% surfactant level shampoo.

| Ingredient | % (w/w) |
| --- | --- |
| TEA lauryl sulfate | 15.5 |
| Sodium laureth sulfate | 6.7 |
| Cocamidopropyl betaine | 1.5 |
| Cocamide DEA | 5.0 |
| Propylene Glycol | 1.0 |
| Disodium EDTA | 0.3 |
| Perfume, Citric Acid, Sodium Chloride | qs |
| Purified Water | qs 100% |

METHOD OF MANUFACTURE

Purified water is weighed into an appropriately sized container in an amount equivalent to about one-fourth of the lot size. The disodium EDTA and citric acid are dissolved and the following ingredients are added in the order of succession and mixed slowly until uniform: TEA lauryl sulfate, propylene glycol, sodium laureth sulfate, cocamide DEA, cocamidopropyl betaine, perfume. If necessary, the ingredients can be mixed to uniformity between additions. Next, purified water is added to within slightly less than the full lot size and mixed until uniform.

The pH and viscosity are adjusted with citric acid and sodium chloride, respectively in a quantity sufficient (qs). If needed, add additional water.

This shampoo, when made according to the method described above, has a pH of about 5.5 and a viscosity of about 5,000 cps. When subjected to preservative challenge testing, it exhibits the kill rates shown below. The preservative challenge testing involves innoculating a sample of the shampoo with the orgainsms shown below at the level indicated and then determining the amount of organism living after the specified time (T) intervals.

| PRESERVATIVE CHALLENGE TEST | | | | |
| --- | --- | --- | --- | --- |
| Organism | T = 7 Days | T = 14 Days | T = 21 Days | T = 28 Days |
| Ps. aeruginosa | <10 | <10 | <10 | <10 |
| E. coli | <10 | <10 | <10 | <10 |
| S. aureus | <10 | <10 | <10 | <10 |
| C. albicans | <10 | <10 | <10 | <10 |
| B. subtilis | 90,000 | 70,000 | 43,000 | 30,000 |
| A. niger | <10 | <10 | <10 | <10 |

| Organism | Inoculation Levels ATCC Number | Level |
| --- | --- | --- |
| Ps. aeruginosa | 9027 | 101,000 |
| E. coli | 8739 | 110,000 |
| S. aureus | 6538 | 101,000 |
| C. albicans | 10231 | 100,000 |
| B. subtilis | 6633 | 100,000 |
| A. niger | 16404 | 110,000 |

These kill rates meet the acceptance criteria for the United States Pharmacopeia (USP), British Pharmacopeia (BP), European Pharmacopeia (EP) and Cosmetic, Tolietries and Fragrence Association (CTFA) preservative challenge testing.

EXAMPLE 2

The following formulation represents an approximately 29% surfactant level shampoo.

| Ingredient | % (w/w) |
| --- | --- |
| Sodium lauryl sulfate | 15.5 |
| Sodium laureth sulfate | 6.7 |
| Cocamidopropyl betaine | 1.5 |
| Cocamide DEA | 5.0 |
| Propylene Glycol | 1.0 |
| Disodium EDTA | 0.3 |
| Perfume, Citric Acid, Sodium Chloride | qs |
| Purified Water | qs 100% |

METHOD OF MANUFACTURE

Purified water is weighed into an appropriately sized container in an amount equivalent to about half the lot size. Sodium lauryl sulfate, citric acid, and disodium EDTA are added and mixed until dissolved. The following ingredients are then added in the order of succession and mixed slowly until uniform: propylene glycol, sodium laureth sulfate, cocamide DEA cocamididopropyl betaine, perfume. If necessary, the ingredients can be mixed to uniformity between additions.

Purified water is added to slightly less than the full lot size and mixed until uniform. The pH and viscosity are adjusted with citric acid and sodium chloride, respectively, as necessary. If needed, additional water is added.

This shampoo, when made according to the method described above, has a pH of about 5.5 and a viscosity of about 28,000 cps.

When subjected to preservative challenge testing, the shampoo passes USP, BP and EP criteria.

EXAMPLE 3

The following formulation represents an approximately 26% surfactant level shampoo.

| Ingredient | % (w/w) |
| --- | --- |
| TEA lauryl sulfate | 14.0 |
| Sodium laureth sulfate | 6.5 |
| Cocamidopropyl betaine | 1.5 |
| Cocamide DEA | 4.5 |
| Propylene Glycol | 1.0 |

| Ingredient | % (w/w) |
|---|---|
| Disodium EDTA | 0.3 |
| Perfume, Citric Acid, Sodium Chloride | qs |
| Purified Water | qs 100% |

METHOD OF MANUFACTURE

The shampoo is prepared in the same manner as Example 1.

When prepared in this fashion, the shampoo has a pH of about 5.5 and a viscosity of about 5,000 cps.

EXAMPLE 4

The following formulation represents an approximately 16.5% surfactant level shampoo.

| Ingredient | % (w/w) |
|---|---|
| TEA lauryl sulfate | 3.7 |
| Sodium laureth sulfate | 7.2 |
| Cocamidopropyl betaine | 2.1 |
| Cocamide DEA | 3.5 |
| Acetamide MEA | 3.0 |
| Perfume, Citric Acid, Sodium Chloride | qs |
| Purified Water | qs 100% |

METHOD OF MANUFACTURE

Purified water is weighed into an appropriately sized container in an amount equivalent to about one-half the lot size. TEA lauryl sulfate and sodium laureth sulfate are added and mixed slowly until uniform. In a separate container, the cocamide DEA, perfume, and acetamide MEA are combined and mixed until clear. This mixture is then added to the first mixture and mixed until clear. The disodium ESTA is added and mixed until dissolved and then the cocamidopropyl betaine is added and mixed until clear.

Purified water is added to slightly less than the full lot size and mixed until uniform. The pH and viscosity are adjusted with citric acid and sodium chloride, respectively. If needed, additional qs water is added.

This shampoo, when made according to the method described above, has a pH of about 5.5 and a viscosity of about 4,000 cps.

When subjected to preservative challenge testing, the shampoo passes the criteria of the USP, BP and EP.

We claim:

1. A conditioning shampoo formulation consisting essentially of
   (a) a fatty alcohol sulfate and/or fatty alcohol-ether sulfate in an amount of at least 10% w/w;
   (b) cocamidopropyl betaine; and
   (c) cocamide diethanolamine;
   wherein the total amount of said (a), (b) and (c) is at least 20% (w/w) and wherein said formulation is free of additional preservatives.

2. The shampoo of claim 1 wherein said (a) is selected from the group consisting of triethanolamine lauryl sulfate, sodium lauryl sulfate or sodium laureth sulfate.

3. The shampoo of claim 2 wherein said (a) is triethanolamine lauryl sulfate and sodium laureth sulfate.

4. The shampoo of claim 1 wherein said (a) (b) and (c) are present in a total amount of about 30% w/w.

5. The shampoo of claim 1 wherein said (b) is present in an amount of from about 0.5 to about 3% w/w.

6. The shampoo of claim 1 wherein said (c) is present in an amount of from about 2 to about 7% w/w.

7. The shampoo of claim 1 wherein said formulation contains about 14% triethanolamine lauryl sulfate, about 6% sodium laureth sulfate, about 1.5% cocamidopropyl betaine, and about 5% cocamide diethanolamine.

8. The shampoo of claim 1 wherein said formulation contains about 16% triethanolamine lauryl sulfate, about 7% sodium laureth sulfate, about 1.5% cocamidopropyl betaine, and about 5% cocamide diethanolamine.

* * * * *